United States Patent [19]

Ishimitsu et al.

[11] Patent Number: 4,937,335
[45] Date of Patent: Jun. 26, 1990

[54] OXA(THIA)ZOLIDINE DERIVATIVES

[75] Inventors: Keiichi Ishimitsu, Odawara; Hiroyuki Imagawa, Yokohama; Tomio Yamada, Hiratsuka; Michihiko Matsuda, Odawara; Yukio Kitagawa, Odawara, all of Japan

[73] Assignee: Nippon Soda Co., Ltd., Tokyo, Japan

[21] Appl. No.: 394,872

[22] Filed: Aug. 17, 1989

Related U.S. Application Data

[62] Division of Ser. No. 186,489, Mar. 18, 1988.

[30] Foreign Application Priority Data

Jul. 29, 1986 [JP] Japan ................. 61-176740

[51] Int. Cl.$^5$ .............................. C07D 277/14
[52] U.S. Cl. ............................ 540/603; 544/133; 544/369; 546/209; 548/188
[58] Field of Search .......... 540/603; 544/369; 546/209; 549/133; 548/188

[56] References Cited

U.S. PATENT DOCUMENTS 4,442,116  4/1984  Iwataki et al. ............... 548/188
4,764,514  8/1988  Ueda ............................ 548/188

Primary Examiner—Donald G. Daus
Attorney, Agent, or Firm—George B. Oujevolk

[57] ABSTRACT

The present invention relates to a compound having the formula

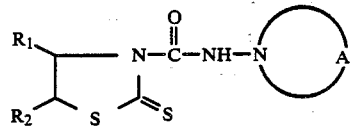

wherein $R_1$ denotes $C_{1-6}$ alkyl radicals; $R_2$ denotes halogen atoms, $C_{1-6}$ alkyl radicals, $C_{1-6}$ haloalkyl radicals, $C_{1-6}$ alkoxy radicals, $C_{1-6}$ haloalkoxy radicals or the phenyl radicals which may be substituted by methylenedioxy radicals;

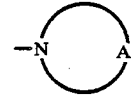

denotes 5–7 member heterocyclic radicals whose ring constituent atoms comprise 2–6 carbon atoms, 0–1 oxygen atom and 1–2 nitrogen atoms and which may be substituted by $C_{1-6}$ alkyl radicals.

1 Claim, No Drawings

OXA(THIA)ZOLIDINE DERIVATIVES

This is a divisional application of U.S. patent application Ser. No. 07/186,489 filed 03/18/88.

TECHNICAL FIELD

The present invention relates to new oxa(thia)zolidine derivatives having an excelling acaricidal activity, their manufacturing processes and the acaricides made therefrom.

BACKGROUND ART

The following compounds which are disclosed in UK Patent 2059961 are known as compounds which like those covered by this invention have a heterocyclic ring containing nitrogen as a substituent of the carbamoyl moiety.

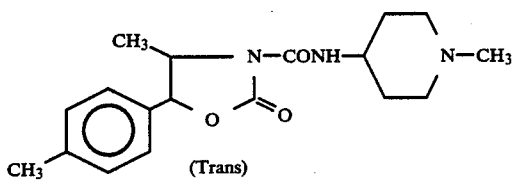

The purpose of this invention is to offer agricultural chemicals which can be advantageously synthesized on a commercial basis and which having positive effects can be used safely.

DISCLOSURE OF INVENTION

The present invention relates to a compounds having the formula

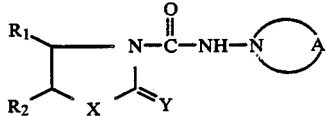 (I)

wherein $R_1$ denotes $C_{1-6}$ alkyl radicals; $R_2$ denotes halogen atoms, $C_{1-6}$ alkyl radicals, $C_{1-6}$ haloalkyl radicals, $C_{1-6}$ alkoxy radicals, $C_{1-6}$ haloalkoxy radicals or the phenyl radicals which may be substituted by methylenedioxy radicals;

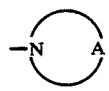

denotes 5-7 member heterocyclic radicals whose ring constituent atoms comprise 2-6 carbon atoms, 0-1 oxygen atoms and 1-2 nitrogen atoms and which may be substituted by $C_{1-6}$ alkyl radicals; X and Y each denote oxygen atoms or sulfur atoms, the method of their manufacture, and the acaricides made therefrom.

BEST MODE FOR CARRYING OUT THE INVENTION

The compounds of this invention can be manufactured in accordance with the following reaction formulas.

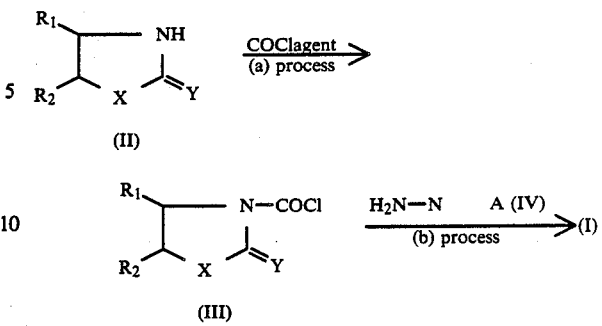

The reactions in the manufacturing process (a) are allowed to proceed for a period of 30 minutes to several hours, in an organic solvent, in the presence of a base, at a temperature from $-20°$ C. to the boiling point of the solvent used, desirably from $0°$ C. to room temperature. For the COCl agent, it is possible to use phosgene, trichloromethyl chloroformate (hereunder called TCF), etc. For the organic solvent can be used benzene, toluene, xylene, THF, chloroform or other ordinary solvents. For the base, pyridine, triethylamine, etc. can be used. After these reactions end, normally product isolation is not made but reactions of the succeeding process are allowed to follow:

The reactions in the manufacturing process (b) are allowed to go for a period of 30 minutes to several hours in an organic solvent, in the presence of a base, at a temperature from $-20°$ C. to the boiling point of the solvent used, desirably from $0°$ C. to room temperature. For the organic solvent, use is made of the similar solvent as used in the manufacturing process (a). Normally, the solvent for the process (a) is employed. For the base, pyridine, triethylamine, etc. may be used, but also usable as such is material amine, expressed in the general formula (IV), in an amount equaling or exceeding 2 moles. After the reactions are ended, ordinary after-treatment is made to obtain specified substance.

The structure of the compounds of this invention was determined by IR, NMR, MASS, etc. In the compounds of this invention, the trans-forms and cis-forms derived from the 4- and 5-positions of the oxa(thia)zolidine ring are present, as are R-form, S-form or other isomers. These isomers are all included in the compounds which this invention concerns.

The following examples illustrate the present invention.

EXAMPLE 1

5-(4-chlorophenyl)-4-methyl-3-piperidino carbamoyl-2-thiazolidone (Compound No. 14)

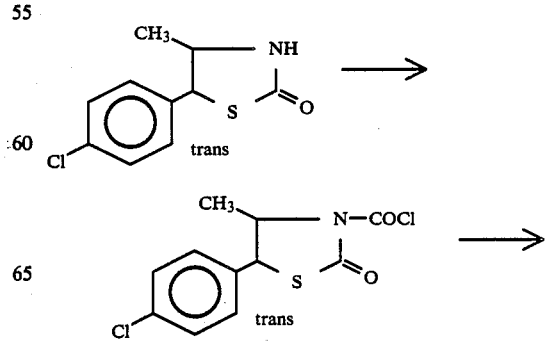

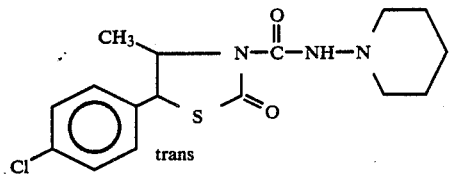

To a solution of 2.3 g of 5-(4-chlorophenyl)-4-methyl-2-thiazolidone and 0.8 g of pyridine in 30 ml of benzene was added dropwise 1.0 g of T.C.F. on cooling. After stirring at the same temperature for 1 hour, 2.0 g of N-aminopiperidine was added to the solution, followed by stirring for 3 hours at room temperature. The reaction mixture was then poured into ice-water, extracted with ethyl acetate, dried with anhydrous magnesium sulfate and concentrated under reduced pressure. The residue obtained was purified by column chromatography on silica gel to give 2.3 g of compound No. 14. mp 92°–93° C.

EXAMPLE 2

4-methyl-5-(4-methylphenyl)-3-morpholinocarbamoyl-2-oxazolidone (Compound No. 6)

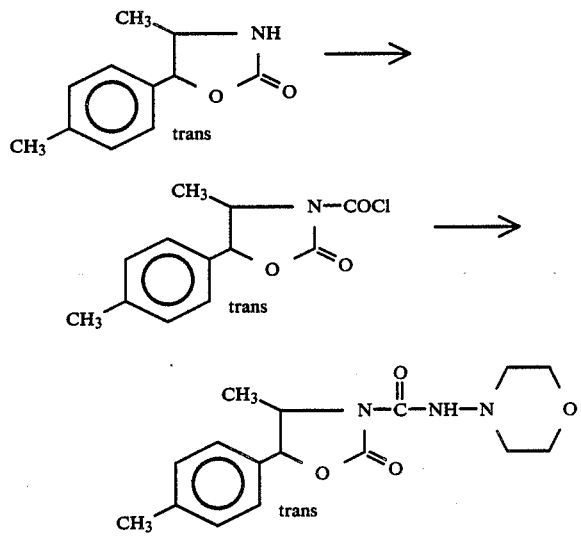

To a solution of 1.9 g 4-methyl-5-(4-methylphenyl)-2-oxazolidone and 0.8 g of pyridine in 30 ml of benzene was added dropwise 1.0 g of T.C.F. on cooling. After stirring at the same temperature for 1 hour, a mixture of 1.0 g of N-aminomorpholine and 1.0 g of triethylamine was added to the solution, followed by stirring for 3 hours at room temperature. The reaction mixture was then poured into ice-water, extracted with ethyl acetate, dried with anhydrous magnesium sulfate and concentrated under reduced pressure. The residue obtained was purified by column chromatography on silica gel to give 2.7 g of compound No. 6. mp 124°–125° C.

EXAMPLE 3

4-methyl-5-(4-methylphenyl)-3-morpholinocarbamoyl-thiazolidine-2-thione (Compound No. 26)

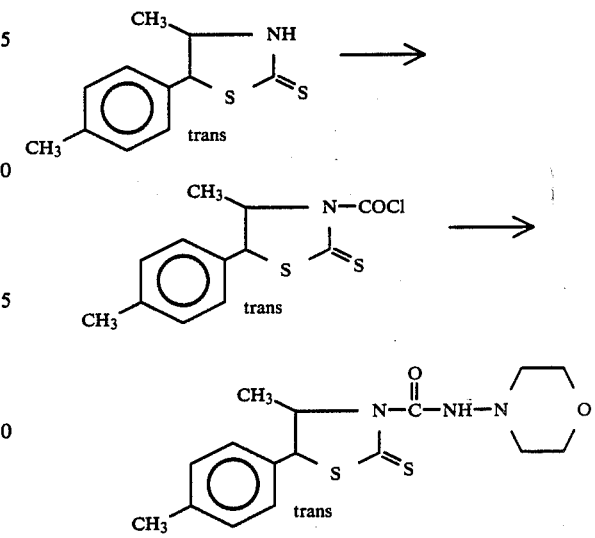

To a solution of 2.2 g of 4-methyl-5-(4-methylphenyl)thiazolidine-2-thione and 0.8 g of pyridine in 30 ml of benzene was added dropwise 1.0 g of T.C.F. on cooling. After stirring at the same temperature for 1 hour, a mixture of 1.0 g of N-aminomorpholine and 1.0 g of triethylamine was added to the solution, followed by stirring overnight at room temperature. The reaction mixture was then poured into ice-water, extracted with ethyl acetate, dried with anhydrous magnesium sulfate and concentrated under reduced pressure. The residue obtained was purified by column chromatography on silica gel to give 3.0 g of compound No. 26. mp 101°–103° C.

Inclusive the above, each compound with the scope of the present invention which can be prepared in analogous method is tabulated in Table 1.

TABLE 1

Structure

R₁ — NCONH—N A
R₂ / X / Y

| Compound No. | $R_1$ | $R_2$ | X | Y | $-N\underset{}{\overset{}{A}}$ | trans/cis | Physical Properties [ ] melting point °C. |
|---|---|---|---|---|---|---|---|
| 1 | $CH_3$ | 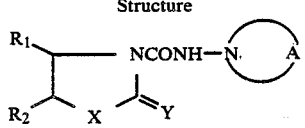 | O | O | —N(piperidine) | trans | (130~131) |

TABLE 1-continued

Structure $$\begin{matrix} R_1 \\ | \\ R_2-X \end{matrix} \begin{matrix} NCONH-N\underset{A}{\frown} \\ \parallel \\ Y \end{matrix}$$

| Compound No. | R₁ | R₂ | X Y | −N⟨A | trans/cis | Physical Properties [ ] melting point °C. |
|---|---|---|---|---|---|---|
| 2 | " | " | " " | −N⟨O (morpholine) | " | (118~120) |
| 3 | " | " | " " | −N⟨N−CH₃ (N-methylpiperazine) | " | (98~100) |
| 4 | " | CH₃−C₆H₄− | " " | −N⟨ (piperidine) | " | (96~98) |
| 5 | " | " | " " | −N⟨ (pyrrolidine) | " | (81~83) |
| 6 | " | " | " " | −N⟨O (morpholine) | " | (124~125) |
| 7 | " | " | " " | −N⟨(CH₃)O(CH₃) (2,6-dimethylmorpholine) | " | (64~65) |
| 8 | " | C₆H₅− | " " | −N⟨O | " | (110~111) |
| 9 | " | CF₃−C₆H₄− | " " | −N⟨ | " | (131~132) |
| 10 | " | 3,4-Cl₂−C₆H₃− | " " | " | " | (179~181) |
| 11 | " | methylenedioxyphenyl | " " | " | " | (90~91) |
| 12 | " | 3,4-(CH₃)₂−C₆H₃− | " " | −N⟨O | " | (116~117) |

TABLE 1-continued

Structure:

$$R_1\text{-CH}(R_2)\text{-CH}(X)\text{-C}(=Y)\text{-NCONH-N}\backslash A$$

| Compound No. | $R_1$ | $R_2$ | X | Y | $-N\backslash A$ | trans/cis | Physical Properties [ ] melting point °C. |
|---|---|---|---|---|---|---|---|
| 13 | " | 4-CH₃-C₆H₄- | " | " | morpholino | cis | (128~129) |
| 14 | " | 4-Cl-C₆H₄- | S | " | piperidino | trans | (92~93) |
| 15 | " | " | " | " | morpholino | " | (145~146) |
| 16 | " | " | " | " | 2,6-dimethylpiperidino | " | $n_D^{24}$ 1.5420 |
| 17 | " | 4-CH₃-C₆H₄- | " | " | piperidino | " | (107~108) |
| 18 | " | " | " | " | hexamethyleneimino | " | (83~85) |
| 19 | " | " | " | " | morpholino | " | (115~116) |
| 20 | " | C₆H₅- | " | " | piperidino | " | (123~124) |
| 21 | " | " | " | " | morpholino | " | (121~122) |
| 22 | " | 4-F-C₆H₄- | " | " | " | " | (144~146) |
| 23 | " | 3-CF₃-C₆H₄- | " | " | piperidino | " | (117~118) |

TABLE 1-continued

Structure:

$$R_1\text{—CH(R_2)—X—C(=Y)—NCONH—}\langle A \rangle$$

| Compound No. | R$_1$ | R$_2$ | X | Y | —N⟨A⟩ | trans/cis | Physical Properties [ ] melting point °C. |
|---|---|---|---|---|---|---|---|
| 24 | " | CH$_3$O—⟨phenyl⟩— | " | " | —N⟨morpholine⟩O | " | (119~120) |
| 25 | " | CF$_3$O—⟨phenyl⟩— | " | " | " | " | |
| 26 | " | CH$_3$—⟨phenyl⟩— | " | S | " | " | (101~103) |
| 27 | " | FCH$_2$CH$_2$O—⟨phenyl⟩— | " | O | " | " | n$_D^{28}$ 1.5250 |

The acaricides covered by this invention contain as active ingredients one or more types of the compounds as expressed by the general formula (1). These active ingredients, which the compounds are, may be used as-produced but normally they are used in any of the forms which ordinary agricultural chemicals can take, namely wettable powder, dust, emulsifiable concentrate, suspension concentrates or other formulations. For additives and carriers are used soybean flour, wheat flour or other vegetable flours, diatomaceous earth, apatite, gypsum, talc, pyrophyllite, clay or other fine mineral powders, when solid formulations are intended.

When liquid formulations are intended, then for solvents are used kerosene, mineral oil, petroleum, solvent naphtha, xylene, cyclohexane, cyclohexanone, dimethylformamide, dimethylsulfoxide, alcohol, acetone, water, etc. A surface active agent may, if necessary, be added in order to give a homogeneous and suitable formulation. The wettable powders, emulsifiable concentrates, flowables, etc. thus obtained are diluted with water into suspensions or emulsions of a prescribed concentration, before they are actually sprayed on plants in the field. In the case of dusts or granules, they are directly applied without further processing.

The concentration of the active ingredient in an pesticidal composition may very according to type of formulation, and is, for example, in the range of 5-70 weight percent, preferably 10-30 weight percent, in wettable powder; 5-30 weight percent, preferably 10-20 weight percent, in emulsifiable concentrate; 1-10 weight percent, preferably 2-5 weight percent in dust; 5-40 weight percent, preferably 10-30 weight percent in suspension concentrate; 1-10 weight percent, preferably 2-5 weight percent in granular formulation.

Needless to say, the compounds which this invention covers are sufficiently effective even if they are applied singly. Since these compounds are weak in adultcidal activity, however, their application in combination with one of more types of compounds having adultcidal activity against mites, parasitic on plants, proves to be remarkably effective. In addition to adultcidally active compounds, one or more types of other agricultural chemicals may also be used in combination with the compounds of this invention.

Typical examples of acaricides or insecticides that can be used together with the compounds of this invention are as follows. Acaricides (fungicides): BCPE chlorobenzilate, chloropropylate, proclonol, phenisobromolate, dicofol, dinobuton, binapacryl, chlorphenamidine, amitraz, BPPS, PPPS, benzomate, cyhexatin, fenbutation oxide, polynactins, chinomethionat, thioquinox, CPCBS, tetradifon, tetrasul, cycloprate, kayacide, kayahope, 3-n-dodecyl-1,4-naphthquinon-2-ylacetate, calcium-oxide polysulfide. Organophosphorus insecticides (acaricides): fenthion, fenitrothion, diazinon, chlorpyrifos, ESP, vamidothion, phenthoate, dimethoate, formothion, malathion, dipterex, thiometon, phosmet, menazon, dichlorvos, acephate, EPBP, dialifor, methyl parathion, oxydemethone-methyl, ethion, aldicarb, propoxur Pyrethroid-type insecticides (acaricides): permethrin, cypermethrin, decamethrin, fenvalerate, fenpropathrin, pyrethrins, allethrin, tetramethrine, resmethrin, pallethrin, dimethrin, proparthrin, prothrin, 3-phenoxybenzil-2,2-dichloro-1-(4-ethoxyphenyl)-1-dichlor-propanecarboxylate
α-cyano-3-phenoxybenzil-2,2-dichloro-1-(4-ethoxyphenyl)-1-cyclopropanecarboxylate
(RS)-α-cyano-3-phenoxybenzil(RS)-2-(4-trichlormethoxypenyl)-3-methylbutylate
(RS)-α-cyano-3-phenoxybenzil(RS)-2-(2-chloro-4-trichloromthylanilino)3-methylbutylate
Machine oils Some examples of the formulations are given below. The carriers, surface-active agents, etc. that are added, however, are not limited to these examples.

EXAMPLE 4

Emulsifiable concentrate

The compound of this invention: 10 parts
Alkylphenyl polyoxyethylene: 5 parts
Dimethyl formamide: 50 parts
Xylene: 35 parts These components are mixed and dissolved and, for use in spraying, the liquid mixture is water-diluted into an emulsion.

EXAMPLE 5

Wettable powder

The compound of this invention: 20 parts
Higher alcohol sulfuric ester: 5 parts
Diatomaceous earth: 70 parts
White carbon: 5 parts These components are mixed and ground to fine powders, which for use in spraying, are water-diluted into a suspension.

EXAMPLE 6

Dust

The compound of this invention: 5 parts
Talc: 94.6 parts
Silica: 0.3 part
Alkylphenyl polyoxyethylene: 0.1 part These are mixed and ground and used as-ground in spraying.

Industrial Applicability:

The tests below show the acaricidal activity of the compounds of this invention.

TEST 1

Control effect on two-spotted spider mite

After being sowed in a 6 cm diameter pot, kidney beans sprouted and 7 to 10 days elapsed, their first leaves were inoculated with 30 female adults of two-spotted spider mite resistant to organophosphous chemicals. In the procedures of the Example 4 above, an emulsifiable concentrate of the compound of the present invention was then water-diluted to an emulsion at a concentration of 31.3 ppm and was sprayed on the inoculated leaves. Three days after spraying, the adults were removed. Concerning the eggs which the adults had deposited during these 3 days, an examination was conducted on the 11th day to see whether they had grown to adults. Thus the control efficacy of the acaricide was determined. The results are as shown in the following Table 2.

The control efficacy was obtained by the following formula.

Control efficacy (%) =

$$\frac{\text{No. of adults in } n\text{-}t^* \text{ area} - \text{No. of adults in } t^{**} \text{ area}}{\text{No. of adults in } n\text{-}t^* \text{ area}} \times 100$$

*$n$-$t$ = non-treated
**$t$ = treated

TABLE 2

| Compound No. | Control Efficacy (%) |
|---|---|
| 1 | 100 |
| 2 | 100 |
| 9 | 100 |
| 10 | 100 |
| 11 | 100 |
| 14 | 100 |
| 15 | 100 |
| 16 | 100 |
| 17 | 100 |
| 19 | 100 |
| 20 | 100 |
| 21 | 100 |
| 22 | 100 |
| 23 | 100 |
| 26 | 100 |
| Compound A* | 0 |

[Structure of Compound A* (trans): 2,4-dimethylphenyl group with N—CONH—(4-methylpiperazinyl) and acetyl substituents]

What is claimed is:

1. A compound having the formula

[Structure showing R1, R2 groups with N—C(=O)—NH—N-A linkage and C=S group]

wherein $R_1$ denotes $C_{1-6}$ alkyl radicals; $R_2$ denotes the phenyl radical which may be substituted by halogen atoms, $C_{1-6}$ alkyl radicals, $C_{1-6}$ haloalkyl radicals, $C_{1-6}$ alkoxy radicals, $C_{1-6}$ haloalkoxy radicals or methylenedioxy radicals;

[Structure: -N-A ring]

denotes a heterocyclic radical selected from the group consisting of piperidino, morpholino, 1-piperazinyl, 1-pyrrolidinyl and 1-perhydroazepinyl which may be substituted by $C_{1-6}$ alkyl radicals.

* * * * *